US00PP26060P3

(12) United States Plant Patent

Bodapati et al.

(10) Patent No.: US PP26,060 P3

(45) Date of Patent: Nov. 10, 2015

(54) *PONGAMIA* TREE NAMED 'K140'

(50) Latin Name: *Pongamia pinnata* (L) Pierre
Varietal Denomination: K140

(71) Applicant: TERVIVA BIOENERGY, Oakland, CA (US)

(72) Inventors: Naidu Bodapati, Oakland, CA (US); Marshall Mackay, Oakland, CA (US)

(73) Assignee: Terviva Bioenergy, Oakland, CA (US)

( * ) Notice: Subject to any disclaimer, the term of this patent is extended or adjusted under 35 U.S.C. 154(b) by 71 days.

(21) Appl. No.: 13/987,126

(22) Filed: Jul. 1, 2013

(65) Prior Publication Data

US 2015/0020251 P1 Jan. 15, 2015

(51) Int. Cl.
*A01H 5/00* (2006.01)

(52) U.S. Cl.
USPC ..... Plt./216

(58) Field of Classification Search
USPC ..... Plt./216
CPC ..... A01H 5/00
See application file for complete search history.

(56) References Cited

PUBLICATIONS

U.S. Appl. No. 13/987,125, filed Jul. 1, 2013, Bodapati et al.
U.S. Appl. No. 13/987,127, filed Jul. 1, 2013, Bodapati et al.

*Primary Examiner* — Kent L Bell
(74) *Attorney, Agent, or Firm* — Dentons US LLP

(57) ABSTRACT

'K140' is a new *Pongamia* tree distinguished by having consistent and abundant production of exceptionally large seed pods, coupled with a very high oil content of the seeds.

7 Drawing Sheets

Latin name of the genus and species of the tree claimed: *Pongamia pinnata* (L) Pierre.

Cultivar denomination: 'K140'.

BACKGROUND OF THE INVENTION

The invention relates to a new and distinct cultivar of *Pongamia* tree (*Pongamia pinnata* (L) Pierre) named 'K140'. 'K140' was discovered by the inventors growing in an urban cultivated area in southeastern Queensland, Australia, wherein it and neighboring trees are grown for shade and other landscape amenities. The parentage of this tree is unknown, as is typical for trees cultivated in landscape plantings of this type.

'K140' has been reproduced asexually through vegetative cuttings.

'K140' has not been made publicly available more than one year prior to the filing date of this application.

SUMMARY OF THE INVENTION

A new and distinct variety of *Pongamia* tree (*Pongamia pinnata* (L) Pierre), named 'K140', which is distinctly characterized by unusual pendulous branches arching downward from a dense, spreading crown, large seed pods with exceptionally large seeds (2.1 g) containing high seed-oil content (41.4%, dry-weight basis) and annual (or nearly so) production of large quantities of pods. 'K140' demonstrates excellent vigor and is reasonably resistant to insect and disease pests.

The original tree (and source of clonal material) was identified and selected primarily on the basis of its consistent production of large and abundant seed pods, coupled with the high oil content (41.4%, dry-weight basis) of its large seeds. This selected individual was assigned identity number 'K140'. Subsequently, branch cuttings were collected from the donor tree and rooted by treating the cuttings with the rooting hormone indolebutyric acid (IBA) using either an aqueous solution of IBA (500 ppm) or a commercially available rooting powder. Dehydration of the cuttings was avoided by placing them in moistened rooting medium within a humid enclosed chamber. Rooting success varies from one collection event to another, which is normal for cuttings from mature trees. Typically 10% or more of the cuttings initiated root development within 3 to 4 weeks. Cuttings were rooted in Brisbane, Australia, as well as in Texas, U.S.A. These asexually propagated rooted cuttings remain true-to-type, and show considerable resemblance among one another, after accounting for differences for variation in overall size of the cuttings from which the individual trees were derived.

Similar to *Pongamia* cultivars 'K128b' (U.S. Patent Publ. No. 2015/0020250) and 'K606' (U.S. Patent Publ. No. 2015/0020252), 'K140' has a strong tendency to produce regular crops of pods each year. Relative to other comparison cultivars, 'K140' is unusual for its exceptionally large seeds (averaging 2.1 g) borne in correspondingly large pods, and its exceptionally high seed-oil content (41%). For example, seeds from *Pongamia* cultivar 'K128b' average 0.88 g and contain approximately 38.5% oil. Pods from 'K140' are further characterized by an acuminate apical tip that is distinctly hooked and pointing away from the pod's ventral suture. The rounded crown of 'K140' is distinguished by its downward arching and pendulous branches. Relative to *Pongamia* cultivars 'K128b' and 'K606', the terminal leaflets of 'K140' tend to be similar in size relative to lateral leaflets from the same leaf. For both 'K128b' and 'K606', terminal leaflets tend to be larger than corresponding lateral leaflets. Finally, 'K140' exhibits distinctive corky plumes subtending leaf nodes from the current year's shoots.

BRIEF DESCRIPTION OF THE DRAWINGS

This new *Pongamia* tree is illustrated by the accompanying photographs, which show the tree's form, branches, foliage, leaves, trunk, pods, and seeds. The colors shown are as true as can be reasonably obtained by conventional photographic procedures.

DETAILED BOTANICAL DESCRIPTION

Figure 1:
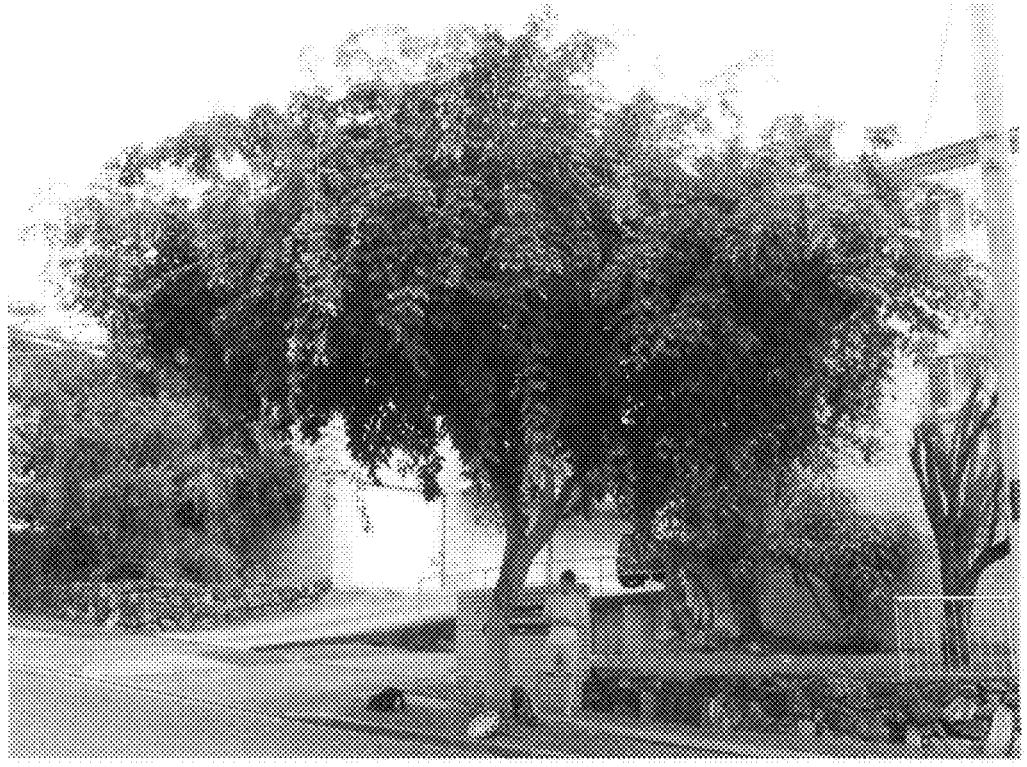
FIG. 1—shows an overview of 'K140' as seen from the street, demonstrating the downward-arching branchlets on the perimeter of the crown. The crown has been periodically pruned to accommodate utility lines.
Figure 2:
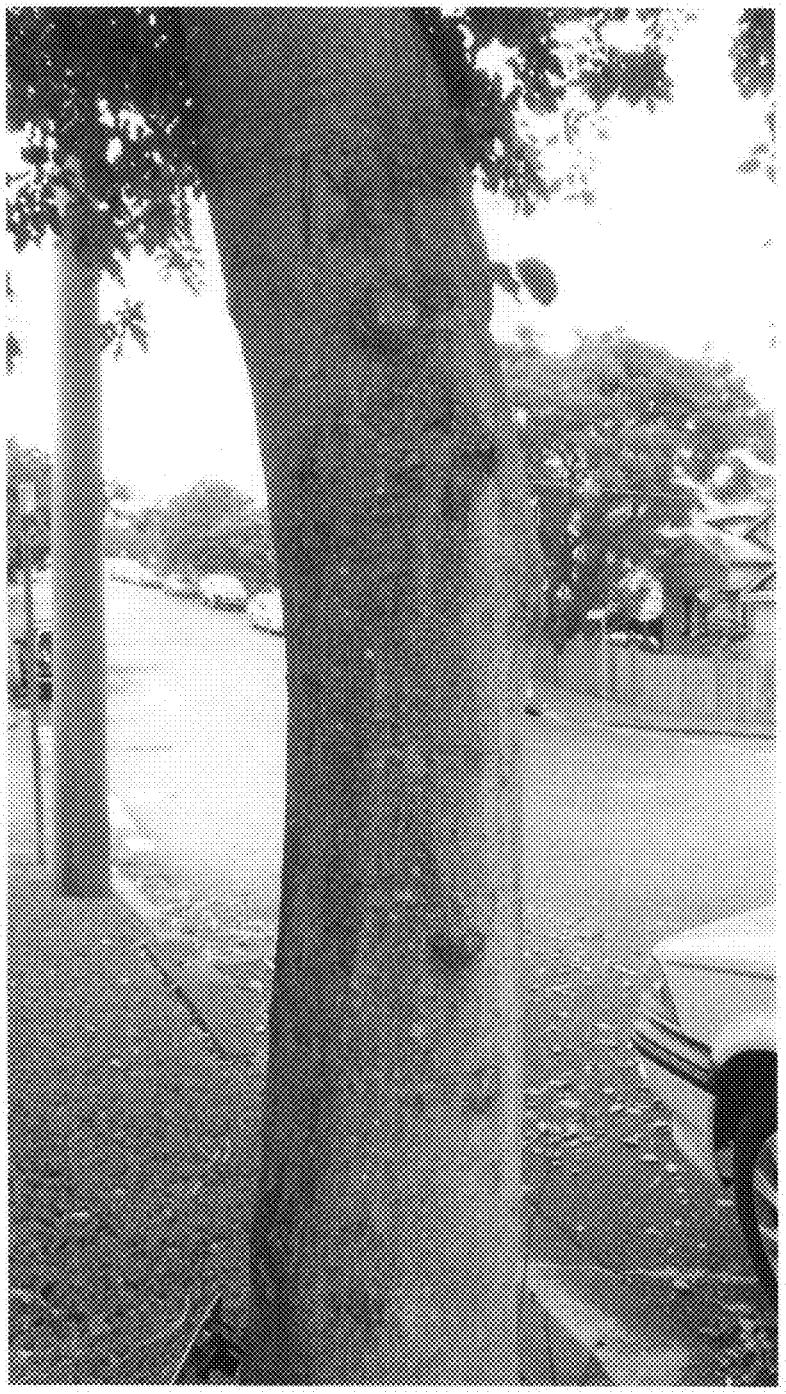
FIG. 2—shows the smooth gray bark on the main trunk. Mottled patches of lighter and darker gray primarily reflect differences in lichen growth.
Figure 3:
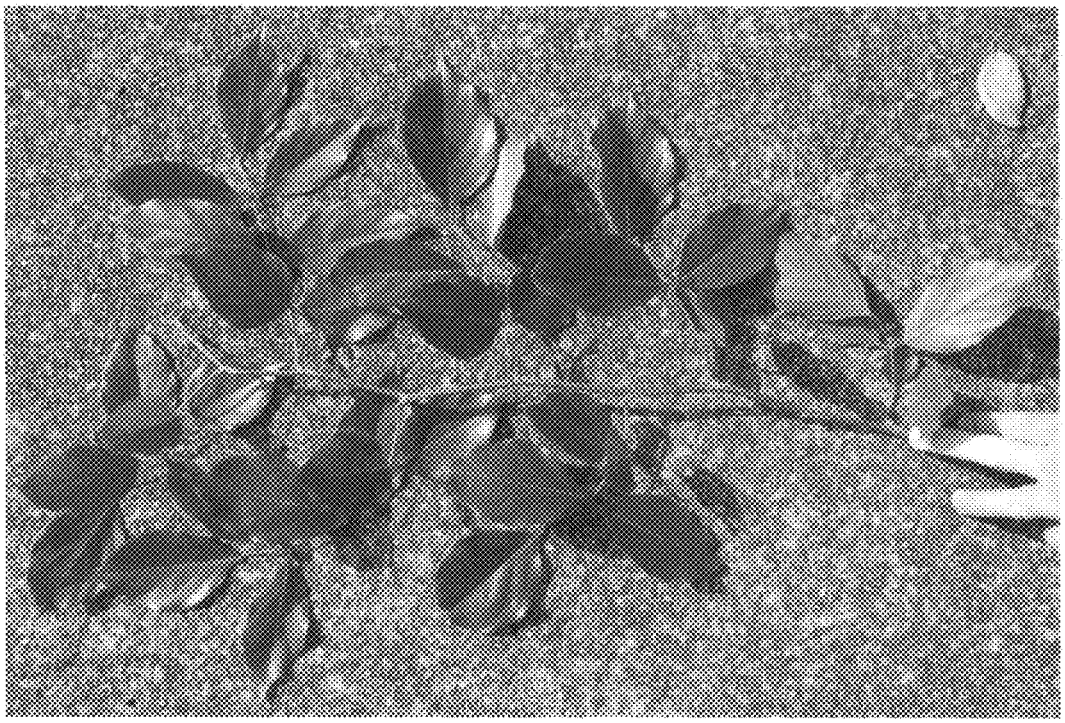
FIG. 3—shows a terminal shoot from the current year's growth. Shown are seven compound leaves along the length of the shoot.
Figure 4:
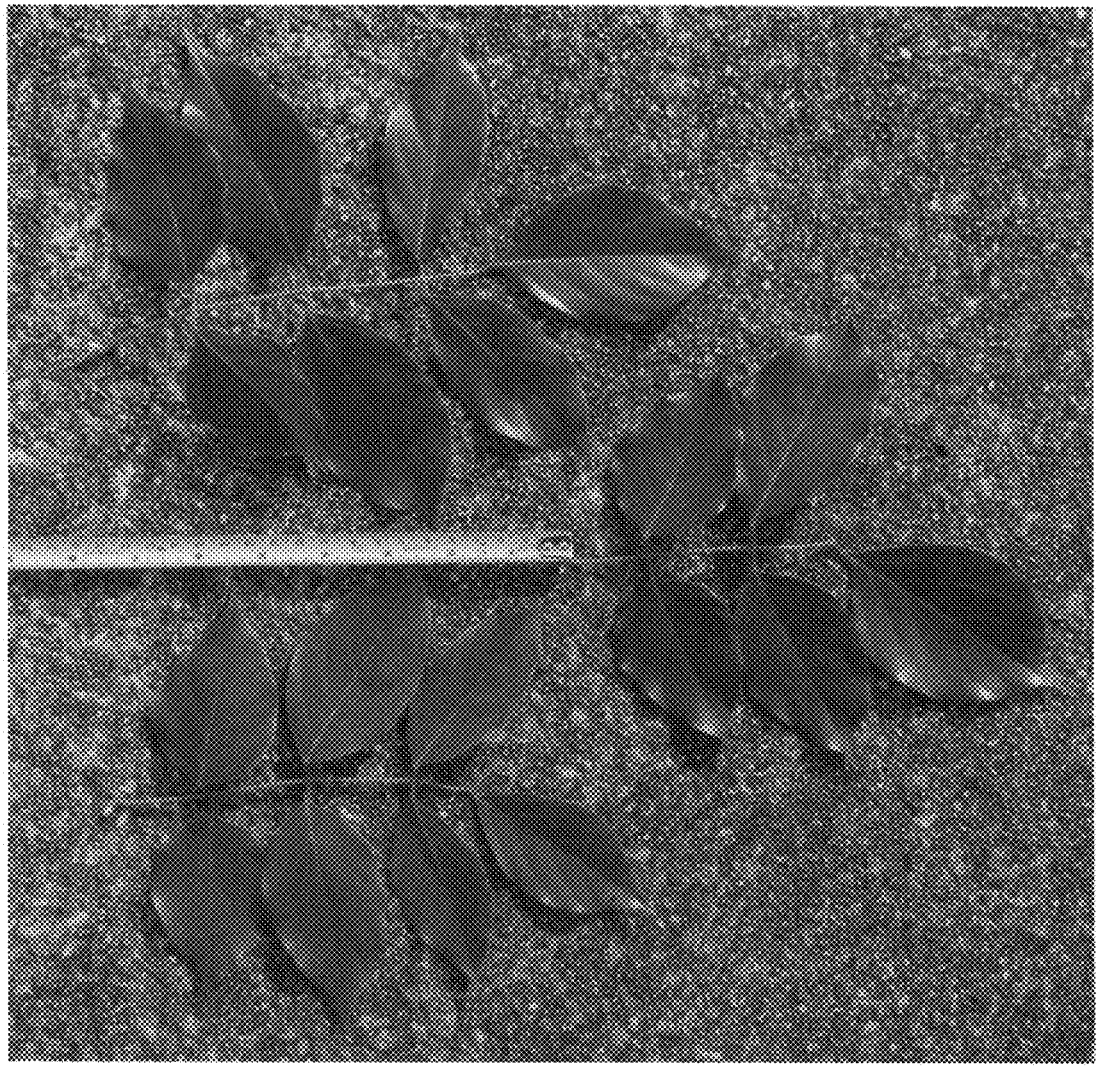
FIG. 4—shows pinnately compound leaves with 5 to 7 leaflets. Leaflets are elliptic to ovate in shape with a cuspidate apex. Leaflet venation tends to be arcuate. The terminal leaflet is roughly equal in size to the lateral leaflets.
Figure 5:
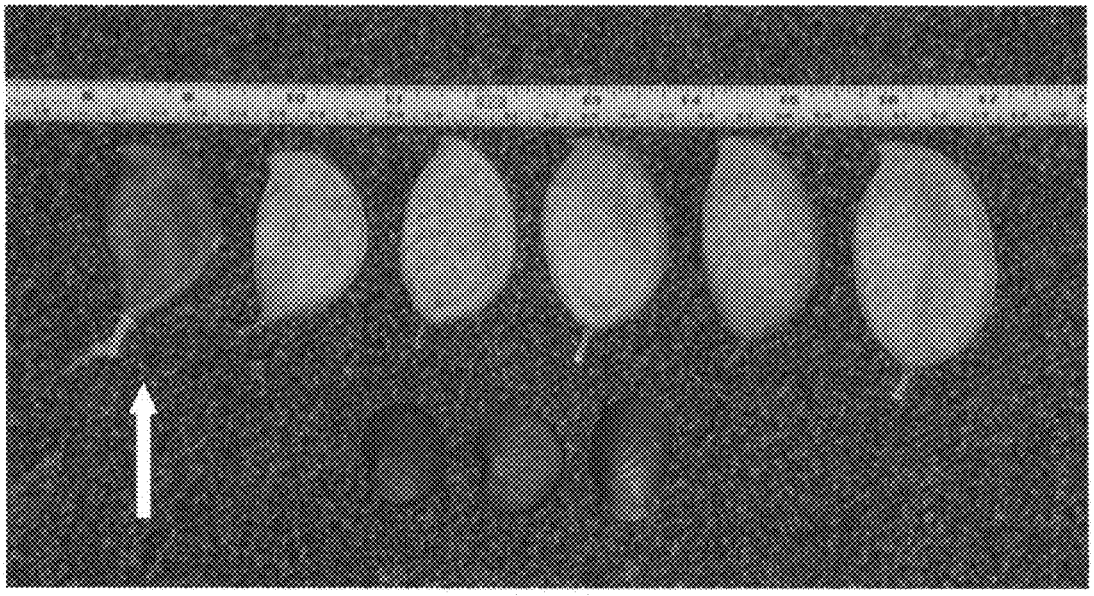
FIG. 5—shows five mature seed pods (aligned in the top row), ready for harvest and 3 seeds (bottom row). Seed pods are bilaterally symmetrical in outline, with an acuminate apical hook pointing towards the left, away from the ventral suture (where developing seeds are attached). Also shown is an immature seed pod (arrow). The reddish-brown seeds (bottom row) are somewhat variable in size. Larger seeds are typically found in larger pods.
Figure 6:
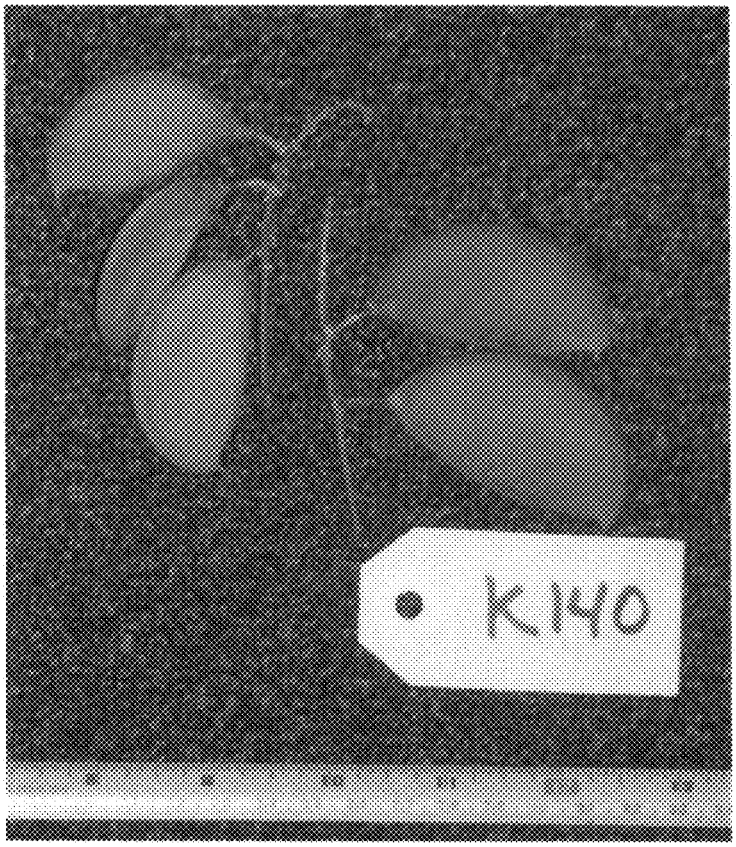
FIG. 6—shows two unbranched fruit clusters showing immature pods attached to their respective central rachis. Most fruiting structures are unbranched, but some branched fruiting structures are also observed.
Figure 7:
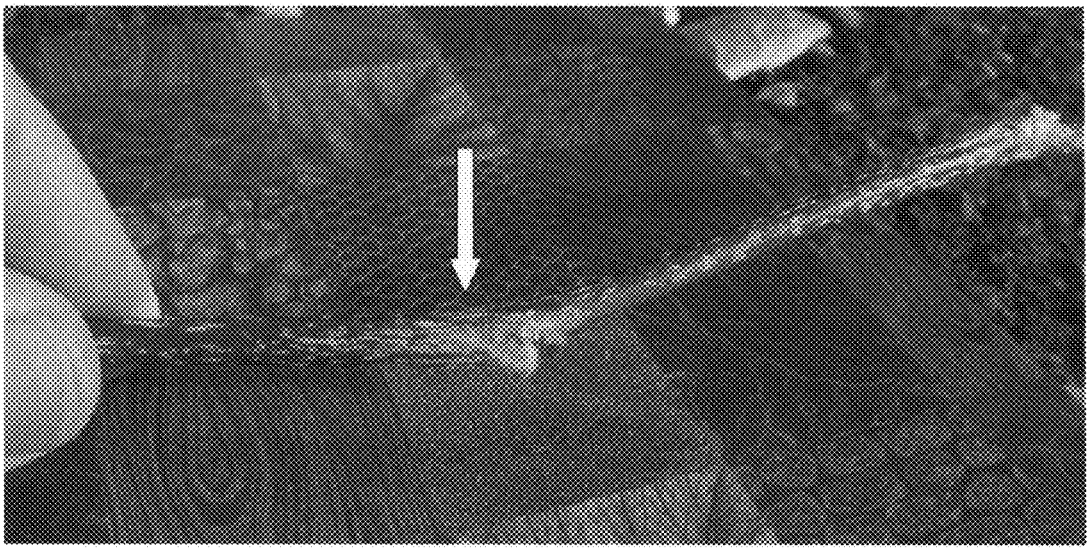
FIG. 7—shows a section of a current year's shoot illustrating corky plumes (arrow) subtending a leaf node.

The following detailed description sets forth the distinctive characteristics of 'K140'. Hereafter, standardized color codes refer to The Royal Horticultural Society (R.H.S.) Mini Colour Chart.

Classification:

*Family*.—Fabaceae.

*Botanical*.—*Pongamia pinnata* (L) Pierre; also called *Millettia pinnata* (L) Panigrahi, *Derris indica* (Lam.) Bennet, *Pongamia glabra* Vent, and *Cytisus pinnatus* (L).

*Common name*.—Pongam tree, or pongam oiltree.

*Cultivar name*.—'K140'.

Plant description:

*Tree*.—Size: Vigorous tree of substantial size and stature, 16 m in height. Crown diameter, measured at the drip-line in two dimensions, is 12.4×12.2 m. Trunk: The arched main stem first branches at a height of 2.4 m from the ground and subsequently branches several more times shortly above. Breast-height diameter of the trunk is 31 cm. Tree crowns and trunks continue to grow as trees age. The trunk shows evidence of epicormic branches that have been removed by pruning. Epicormic shoots can reach 50 to 120 cm in length. Bark: Smooth, grey, with lighter grey flecks and some mottling. Form: Decurrent crown form, with deep-green foliage. Outer pendulous branches are distinctly downward-arching and drooping. The crown has been modestly pruned periodically to prevent unwanted interference with overhead utility lines.

*Branches*.—The largest branches are nearest the ground, located just under 2.4 m from the ground. Their color closely resembles the color of the main stem. These larger branches range from 2 to 10 m in length with a typical length of 4 m. Branching habit: Many branched limbs. Growth and size of lateral branches are considerably less than that of the main branches. Many smaller branches occur higher in the crown. Buds and Shoots: Terminal buds are absent. Young shoots emerge from naked lateral buds, with the most distal bud giving rise to a terminal shoot. Buds are hemispherical and range from 4.2 to 4.6 mm wide at their bases. Buds protrude outward 2.6 to 3.4 mm from the stem and are 1.6 to 2.0 mm thick. The typical bud color is strong yellowish green (RHS 144A) and can be deep yellowish green (RHS 141A) on herbaceous epicormic shoots in full shade. Terminal shoots: The seasonal elongation of terminal shoots is substantial. In the outer portions of the crown, branches are long and slender, and distinctly downward arching. Such terminal shoots range from 5.9 to 8.5 mm in diameter and can be 3 to 4 m long in the outer crown where they droop downward. Stem internodes between leaves are long, averaging 6.7 cm. Lateral shoots: Seasonal elongation of lateral shoots is considerably shorter than for terminal shoots, ranging from about 4 to 20 cm. Diameters of lateral shoots range from 4.9 to 8.5 mm. Shoot and twig surfaces: Woody twigs have leaf scars that are 5.5 to 6.0 mm wide, showing traces of three vascular bundles. The central scar tends to have a border that is less distinct than the outer two. The youngest shoots are distinctly green and flexible, with no lenticels apparent to the naked eye. As shoots mature, their color shifts from green to tan and prominent lenticels become visible as raised light-colored corky circles approximately 1.5 mm in diameter. Distinctive corky plumes subtend both sides of the leaf nodes on the current year's shoots.

*Leaves*.—Pinnately compound leaves bearing typically 5 to 7 deep-green leaflets with entire margins. Leaves are arranged alternately along the stem. Size and shape: The outline of a compound leaf is roughly oval to elliptic, with a length of 19.7 to 27.5 cm (average 23.7 cm) and a width of 15.0 to 23.0 cm (average 19.2 cm). Leaflets: Blades of individual leaflets range from elliptic to (less frequently) ovate in shape with a cuspidate apex and acute bases. Blades of terminal leaflets range in width from 4.5 to 7.0 cm (average 5.8 cm) and in length from 7.9 to 11.4 cm (average 9.5 cm). The smallest leaflets on a leaf tend to be basal, ranging in width from 3.1 to 5.6 cm (average 4.5 cm) and in length from 4.9 to 9.3 cm (average 7.1 cm). Leaflet color, surface, and texture: Leaflets are glabrous on both abaxial and adaxial surfaces. The adaxial surface is moderate olive green (RHS 137A), and the abaxial surface is deep yellowish green (RHS 141A) and less glossy. Young leaves exhibit a strikingly glossy cuticle on their adaxial surface and can be strong yellowish green (RHS 144A) on both surfaces. Leaflets turn darker (towards moderate olive green, RHS 137A) as they age and become increasingly sclerophyllous. Stipules: A pair of small stipules subtends the youngest leaves on a shoot. They remain for only a short duration before they dehisce.

*Flowers and inflorescences*.—Hermaphroditic florets are borne on an indeterminate inflorescence. Inflorescence structure: Several florets are clustered into a fascicle node, which are more-or-less evenly distributed along a rachis. The entire inflorescence is a pseudoraceme. Most inflorescences are unbranched, but some are branched. Position in crown: As many as 3 to 4 inflorescences per branch are borne in the basal leaf axils of the current year's vegetative flush, near the distal end of the prior year's shoot growth. Inflorescences are observed on both terminal and lateral shoots. An average unbranched inflorescence encompasses 35 to 45 florets, averaging 38. Branched inflorescences encompass up to 63 florets. Flower clusters tend to be most common towards the outer surface of the crown. Florets: Emerge acropetally from an ovoid calyx. Zygomorphic florets consist of 5 pinkish-white petals: 2 keel, 2 wing, and a standard (or banner) petal. Flowering period: Relative to other *Pongamia* trees in the general area, 'K140' tends to flower about mid-range into the flowering period (from November to December in southeastern Queensland, Australia).

*Fruits*.—Seed pods usually bear a single seed. An underdeveloped (and much smaller) seed is also observed in some pods. Shape and color: Developing fruits first appear as dark-green flattened pods, expanding in size into lighter green and eventually tan-colored woody pods. Crown distribution: Pods can occur throughout the crown, but are most prevalent towards the outer portions of the crown. Fruit clusters: Pods occur in clusters of 1 to 4 in poorer seed years, and 2 to 10 in better seed years. Pods within a cluster are connected by the rachis of the inflorescence from which they developed. Dimensions: Pods are exceptionally large, ranging in size from 42-62 mm long, by 27 to 38 mm wide, by 8 to 11 mm thick, averaging 50×30×10 mm. Bilaterally symmetrical pods range in shape from oval to half-moon and are somewhat flattened along the dorsal side. The acuminate apical hook points away from the ventral suture (where developing seeds are attached). Intact pods (i.e. with seeds) average 4.2 g in weight. Fruits begin to ripen in late October (in southeastern Queensland, Australia), about 10 months after flowering.

*Seeds*.—Typically borne singly in pods. Sometimes an aborted (and much smaller) seed occurs alongside a fully-formed seed. Seed coat: Seeds are covered by a thin seed coat that is usually dark- to reddish-brown. Seed size: Exceptionally large seeds in a size range from 22 to 29 mm long, by 17 to 24 mm wide, by 6 to 9 mm thick, averaging 25×20×7 mm. Average seed weight is 2.1 g. Seed oil: Oil content is higher than average, relative to other *Pongamia* trees, at 41% oil on a dry-weight basis. Nut crop: Regular bearer. Crop frequency: Most *Pongamia* trees rarely produce abundant nut crops across multiple years, instead bearing fruit biennially or less frequently. 'K140' is unusual in that it bears fruit and seeds during most years. Ripening: Fruit ripening begins in late October and extends into December. If undisturbed, pods remain in the crown for several weeks after they ripen.

What is claimed is:

1. A new and distinct variety of *Pongamia pinnata* (L) Pierre tree called 'K140' as illustrated and described herein.

* * * * *